ions, p. 2123, 1962.

United States Patent

Rosencwaig

[11] 3,948,345
[45] Apr. 6, 1976

[54] METHODS AND MEANS FOR ANALYZING SUBSTANCES

[76] Inventor: Allan Rosencwaig, 92 Royal Drive Apt. 338, Piscataway, N.J. 08854

[22] Filed: June 15, 1973

[21] Appl. No.: 370,526

[52] U.S. Cl.................. 181/.5; 73/24; 73/15 R; G10K/10/00
[51] Int. Cl.²............................................ G10I 1/10
[58] Field of Search............ 181/.5 R, .5 AG, .5 NP; 256/83.3 H, 83.3 UV; 250/343; 73/15, 24, 67.2; 179/100.41 B

[56] References Cited
UNITED STATES PATENTS

| | | | |
|---|---|---|---|
| 2,928,069 | 3/1960 | Petermann | 179/100.41 B |
| 3,322,231 | 5/1967 | Gearnay | 181/.5 R |
| 3,532,181 | 10/1970 | De Maria | 181/.5 R |

OTHER PUBLICATIONS

White, "Generation of Elastic Waves by Transient Surface Heating, Journal of Applied Physics," Dec., 1963, p. 3559.
White, "Elastic Wave Generation by Electron Bombardment or EM Wave Absorption," Communications, p. 2123, 1962.
De Maria, "Picosecond Laser Pulses," Proceedings of the IEEE, Vol. 57, No. 1, 1969, p. 2.
Bell, "Upon the Production of Sound by Radiant Energy," 1881, pp. 510–528, Philosophical Mag., Vol. 11.

*Primary Examiner*—Maynard R. Wilbur
*Assistant Examiner*—N. Moskowitz
*Attorney, Agent, or Firm*—Lerner, David, Littenberg & Samuel

[57] ABSTRACT

In the method and means disclosed, an energy source applies energy of varying magnitude, to a substance being tested, and in a sufficient amount to produce detectable variations in a surrounding fluid. The frequency of the energy is varied. A pickup in the vicinity of the sample responds to the detectable variations and produces electrical signals corresponding to the detected variations. A display indicates the intensity of the electrical signals at the different energy frequencies.

13 Claims, 21 Drawing Figures

METHODS AND MEANS FOR ANALYZING SUBSTANCES

BACKGROUND OF THE INVENTION

This invention relates to methods and means for analyzing substances, and particularly to methods and means for analyzing characteristics of solid and quasi-solid substances.

Solids are generally analyzed by optical transmission methods. However, these methods are unsuitable for studying inorganic or organic materials which occur as polycrystalline powders or are very opaque. Presently, such materials are studied by reflectance methods. However, the latter are somewhat cumbersome and inaccurate.

An object of the present invention is to overcome the foregoing problems.

Still another object of the invention is to improve methods and means for analyzing solid and quasi-solid substances.

Still another object of the invention is to provide methods and means for spectrum analysis of solid substances.

SUMMARY OF THE INVENTION

According to a feature of the invention, these objects are obtained, in whole or in part, by producing energy absorption spectra. This is done by detecting the signals which are established, between a substance being tested and a surrounding fluid, by a source of radiant energy whose amplitude is varied and whose frequency is scanned, and indicating the intensity of the signals at different frequencies of the energy impinging on the sample. In one embodiment the frequency of the energy is continuously scanned.

According to another feature of the invention, the signals are detected by locating an acoustic resonator, tuned to the frequency at which the energy amplitude is modulated, in the fluid near the substance being tested, and transducing the resulting acoustical energy into electrical signals which are caused to vary as the frequency of the energy is changed.

According to another feature of the invention, the fluid surrounding the substance or sample being tested is a gas, such as air.

According to another feature of the invention, the energy is in the form of light and the amplitude modulation is performed by interrupting the light such as by chopping or pulsing.

According to another feature of the invention, the acoustic resonator for detecting the cyclic heat flow between the solid and surrounding fluid is in the form of a resonant tube having a length equal to half the wavelength of the sound wave traveling in the tube.

According to yet another feature of the invention, a microphone is mounted on the resonant tube.

According to yet another feature of the invention, the microphone is in the form of a foil electret mounted on the tube. Preferably, the tube is composed of a metal such as aluminum and forms a capacitor electret microphone with the foil electret. Electrical connections are made to the tube and the metallized side of the foil electret.

According to another feature of the invention, the foil is a mylar or teflon film, metallized on one side and charged by electron implantation on the other side. The metallized side of the foil electret is placed away from the tube.

According to another feature of the invention, the surface of the tube under the electret is ridged to minimize the surface contact between the electret and the tube and thereby prevent the metal surface of the tube from reducing the surface charge on the electret. According to a feature, the ridges are only 0.001 inch high so as to provide a necessary small air gap between the electret foil and the surface of the tube.

According to another feature of the invention, the tube is perforated beneath the electret so that the electret can respond to changes in pressure in the fluid within the tube.

According to another feature of the invention, the acoustical signal detected by the microphone is demodulated, preferably in a lock-in amplifier, to produce a DC signal.

According to another feature of the invention, the resonator and the microphone form part of a cell having an entrance window that directs the modulated and scanned energy to the sample being tested.

According to another feature of the invention, a second apparatus, such as a cell corresponding to the first cell, subjects a reference black body such as carbon black or gold-black sample to a portion of the frequency-varied, or scanned, and amplitude-modulated energy and, after the output from the microphone of the second cell is demodulated to produce a DC signal, a divider divides the demodulated output of the first cell apparatus by the demodulated output of the second apparatus so as to obtain a normalized signal that varies with the frequency of the energy applied.

According to another feature of the invention, a suitable X-Y display system displays the resulting frequency spectrum produced by the signals.

According to another feature of the invention, the demodulated or divided DC voltages are converted to pulse signals in a voltage-to-frequency converter and displayed in a multichannel analyzer.

According to still another feature of the invention, the sample to be tested is mounted on the inside of an exit window in the cell which exit window is placed at one axial end of the tube while the entrance window is located on the other axial end of the resonant tube.

These and other features of the invention are pointed out in the claims. Other objects and advantages of the invention will become evident from the following detailed description when read in light of the accompanying drawings.

DETAILED DESCRIPTION OF PREFERRED EMBODIMENTS

Figure 1:
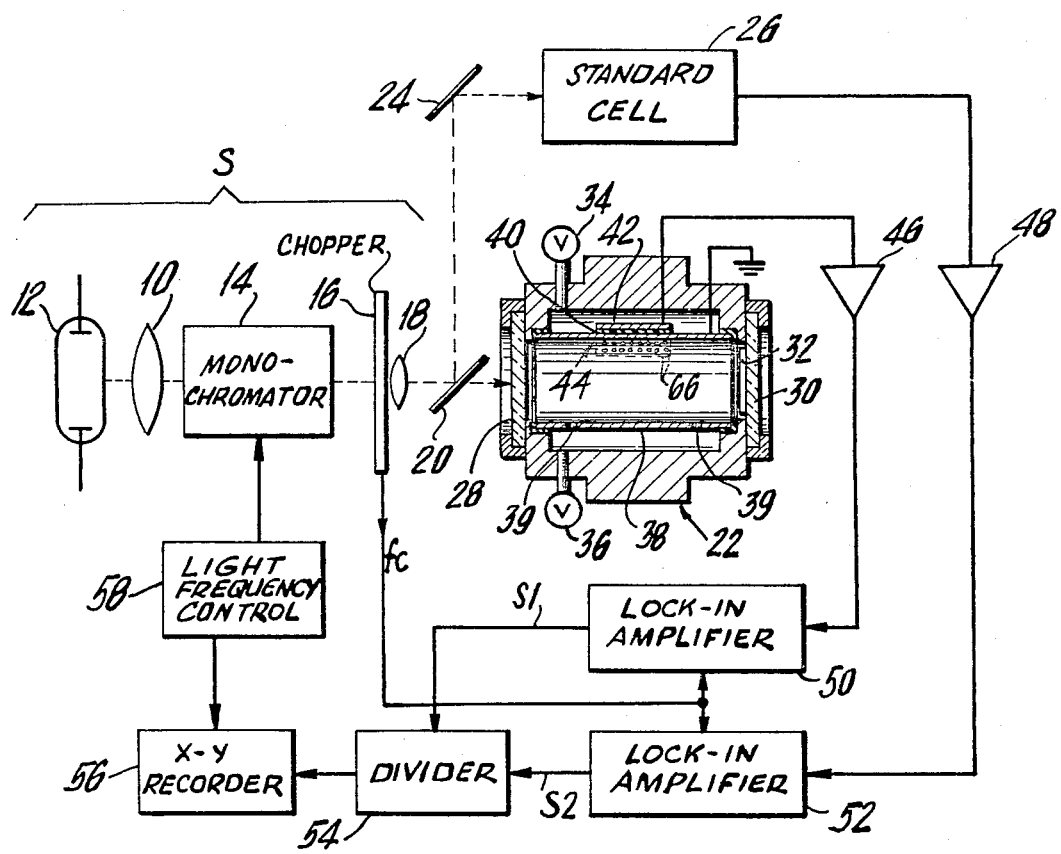
FIG. 1 is a partly schematic block diagram of a system features of the invention.

In FIG. 1 a lens arrangement 10 directs the light output of a Xenon lamp 12 toward a variable monochromator 14 which emits a light beam having a selectable single color, at any moment. The color is time varied along the visible spectrum. Thus the monochromator emits a beam propagating light along a narrow but varying band of frequencies. A chopper 16 chops the beam, by alternately blocking passage of the light and permitting passage of the light, at a frequency $f_c$. A lens system 18 collimates the beam. The elements 10 to 18 form a scanned and modulated or chopped energy source S. The chopper is arranged to produce sinusoidal variation in the light. However this variation can be considered as a sequence of light pulses.

A beam splitter 20 allows half of the chopped light beam to pass to a first photoacoustic cell 22 and reflects the other half of the chopped beam toward a mirror 24 that reflects it toward a photoacoustic cell 26.

One portion of the thus split-off, chopped, light beam enters the cell 22 through a quartz window 28. The latter transmits the beam toward a quartz exit window 30 and onto a solid sample 32 to be analyzed. The sample may be in the form of a powder. A transparent adhesive tape having adhesive on both faces holds the sample 32 in place.

The chopped light impinging upon the solid sample 32 generates sound waves, having a frequency equal to the chopping frequency in the gas surrounding the sample. The sound intensity has been measured as being inversely proportioned to the chopping frequency. The light on the sample 32 alternately adds energy to the sample and allows it to emit energy. Each pulse of light from the chopper effectively heats the sample and each time interval between the pulses gives it an opportunity to cool.

This produces a cyclic expansion and contraction of the sample and a cyclic flow of heat out of the solid sample 32 to the gas surrounding the sample. This produces cyclic displacement and cyclic heating of a layer of the surrounding gas and this, in turn, at least in part acts as a source of sound waves. Preferably, the gas in the cell 22 is air at atmospheric pressure. Other gases may be pumped in and maintained by two valves 34 and 36 at a high pressure. The gas should exhibit a high sound propagating velocity, a low heat capacity and a high expansion coefficient. According to an embodiment of the invention, the valves 34 and 36 are eliminated and the cell communicates with the ambient air.

The sound waves are generated at least in part by the cyclic heat flow and cyclic displacement of the sold sample. These sound waves excite an air column formed by resonant tube 38 whose length equals L/2 and which is mounted with one end near the sample 32. In this case L is the wavelength of the sound waves and equal to $v/f_c$ where $v$ is the speed of the propagation of sound within the gas and $f_c$ the chopping frequency of the chopper 16 in cycles per sec. The resonant tube 38 is made of aluminum or steel. Openings 39 in the tube maintain approximately equal pressures inside and outside the tube, thus allowing the gas pressure in the cell and the resonant tube to be varied at will.

Covering an arc of about 90° and about one-third of the axial length of the tube 38 is a foil electret 40 in the form of a teflon film coated on one side with an aluminum layer 42 and implanted on the side facing the tube 38 with electrons. The electret in conjunction with the aluminum tube and the layer 42 acts as a sensitive electret microphone generally designated 44. The tube 38 is grounded and the aluminum layer 42 of the electret 40 forms the hot side of the microphone 44.

The resonant tube responds to the sound waves produced in the layer of gas surrounding the solid 32 illuminated with chopped light. At any moment the magnitude of the cyclic flow of heat between the sample 32 and the surrounding gas and the magnitude of the cyclic expansion of the solid and hence the magnitude of the sound waves, is a function of the solid sample's ability to absorb the frequency of light passed at that time by the monochromator 14.

The second photoacoustic cell 26 corresponds to the cell 22, except that the solid sample 32 is composed of a black standard such as carbon black or gold black. Standards such as carbon black or gold black absorb light uniformly and thus any distinguishing features or structures in the spectra of these compounds correspond to changes in the magnitude of the light entering the cell. Thus, the electret microphone of the cell 26 produces an output corresponding in intensity to the ability of the carbon black within the cell 26 to absorb the same frequency of the monochromator.

Preamplifiers 46 and 48 amplify the outputs of the electret microphone 44 and the corresponding microphone in the cell 26. A demodulating lock-in amplifier 50 produces a DC output signal S1 corresponding to the amplitude of the output of the preamplifier 46. Similarly, a demodulating lock-in amplifier 52 produces a DC output signal S2 corresponding to the output of the preamplifier 48. The lock-in amplifiers are tuned amplifiers which respond to the frequency of the chopper 16 and may have their phases manually adjusted. Such lock-in amplifiers are available for this purpose from Princeton Applied Research Corporation of Princeton, N.J. as models HR-8. The signal S1 from the lock-in amplifier 50 represents the ability of the sample 32 to absorb light of the frequency determined by the monochromator 14 as detected by the microphone 44. The output signal S2 of the lock-in amplifier 52 represents the corresponding uniform ability of a black body in the cell 26. A divider 54 divides the signal S1 by the signal S2. The divided output S1/S2 thus represents a normalized measurement of the ability of the sample 32 to absorb light. An X-Y recorder 56 records the divided value S1/S2 on its vertical or Y-axis. The normalized measurement eliminates the effect of variations in the intensity of the lamp 12 at various frequencies.

The output is moved along the X-axis by a light frequency control 58 which also changes the frequency of the beam emitted by the monochromator 14. According to an embodiment of the invention, the control 58 forms part of the monochromator.

Figure 2:
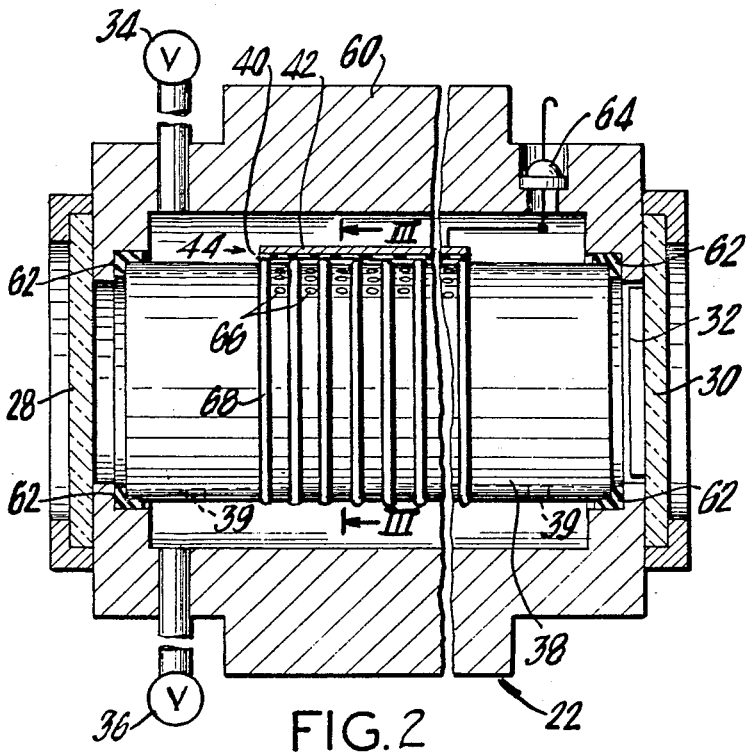
FIG. 2 is a cross-sectional view of a cell of the system shown in FIG. 1.

FIG. 2 illustrates details of the cell 22. Here, the cell walls 60 support the tube 38 by means of sleeves 62. An electric feed-through 64 composed of an insulator and a conductor is ultimately connected to the layer 42.

Figure 3:
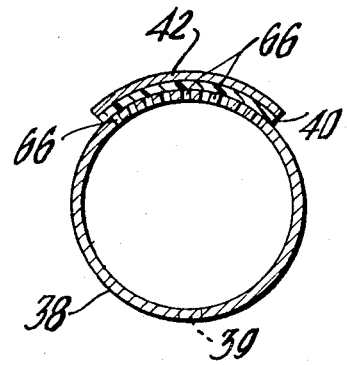
FIG. 3 is a section III—III of FIG. 2.

FIG. 3 illustrates details of the tube 38 and represents an end view section of the tube 38 in FIG. 2. The electret 40 covers one-hundred-forty holes 66 passing radially through the tube 38. The holes 66 form ten circumferentially extending rows of fourteen holes each. The circumferential extent of the rows is 90°, and all the holes are covered by the electret 40. Separating each of the ten rows of holes from each other are circumferential ridges 68. The electret 40 and its aluminum layer 42 are shown with a thickness that is somewhat exaggerated. According to an embodiment of the invention, the teflon electret is 0.5 mil thick. The aluminum film 42 may be less than 0.1 mil thick.

It has been discovered that the electrical signal from the electret microphone is inversely proportional to the chopping frequency. Because the frequency of the output is inversely proportional to the chopping frequency, and because microphones generally have low sensitivity at less than 100 Hz, the microphone 44 is structured for high sensitivity at frequencies between 100 and 1,000 Hz.

The resonant tube 38 has a cross section only slightly larger than the area of illumination of the beam, and highly reflecting surfaces both optically and acoustically. The windows 28 and 30 are transparent optically but highly reflecting acoustically. According to an embodiment of the invention, the tube 38 is made of stainless steel rather than aluminum. The structure 60 is made of stainless steel.

The ridges 68 between the rows of holes 66 behave as spacers to provide an air gap between the electret 40 and the body of the metal tube 38. The ridges and air gap minimize the surface contact between the foil electret and the tube. This prevents the tube 38, which operates as the ground electrode for the electret microphone 44, from reducing the charge embedded in the teflon electret. Embedding of the charge may be accomplished by electron bombardment. The air gap is also necessary to allow the combination of the tube and air and electret to form a capacitor.

The charge embedded in the teflon electret 40 sets up a surface charge on the tube 38 and the presence of these two charges, separated by the air gap formed by the ridges, establishes a bias for the variable capacitance that forms the electret microphone 44. As the distance between the electret 40 and the tube 38 is changed by acoustical pressure changes within the tube, the voltage between the electret and the tube changes, and furnishes an AC electrical signal of acoustic frequency. The capacitive load at the output of the microphone is less than the capacitance of the microphone itself in order to achieve a reasonable signal.

Figure 4:
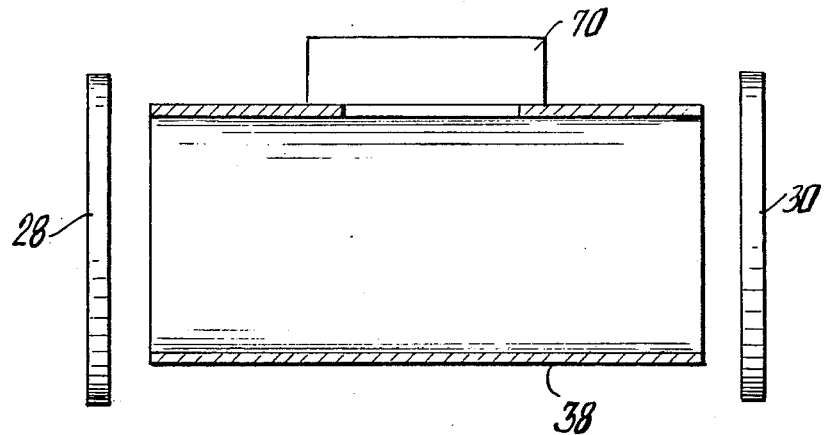
FIG. 4 is a schematic presentation of a cell suitable for replacing the cell of FIG. 1, and embodying features of the invention.

According to another embodiment of the invention, any sensitive commercial microphone 70 is used and incorporated into the side of the tube 38 as shown in FIG. 4.

According to an embodiment of the invention, the tube 38 is made out of stock aluminum tubing having a 1.0 inch outside diameter and a 0.92 inch inside diameter. The aluminum is polished. The length of the tube is 2.60 inches long and holes 66 begin 0.80 inches from one end of the tube and extend 1.0 inches axially along the tube. The circumferential ridges 68 are 1 mil high and 25 mils wide and 50 mils in diameter. Circumferentially the holes are 100 mils apart.

According to one embodiment of the invention, the Xenon lamp 12 is a Hanovia IKW lamp and the monochrometer is a Jarrel-Ash 82–410. The preamplifiers are low-noise high-input impedance preamplifiers, while the lock-in amplifiers are Princeton Applied REsearch model numbers HR-8.

The operation of the device in FIG. 1 may be summarized as follows: The lens arrangement 10 and the Xenon lamp 12 produce a light beam whose band pass is limited to "one" color by the monochrometer 14 and whose amplitude is pulsed by the chopper 60. The beam splitter 20 and mirror 24 divides the resulting beam into two beams and directs each to the photoacoustic cell 22 and 26.

In the photoacoustic cell 22, the chopped beam passes through the entrance window 28 and strikes the solid sample 32 to be tested on the inside of the exit window 30. The energy in the chopped light causes the solid sample to produce a cyclic heat flow and cyclic relative movement with air or other gas within the cell 22. The resulting acoustic expansion and contraction of the surrounding gas from the change in the heat output and expansions of the sample 32 causes acoustic resonance of the gas column in the tube. The resulting sound waves vibrate the electret 40 of the microphone 44 and hence change the capacitance between the foil 42 and the tube 38. This produces an output amplified by the high-input impedance, low-noise preamplifier 46. A similar process occurs in the cell 26 with a carbon black sample. The lock-in amplifiers 50 and 52 in effect select from the total microphone signal, that part with the same frequency as the chopping frequency and demodulate this alternating signal from the electret microphones in the cells 22 and 26 and the resulting DC signals are divided so as to produce normalized measurement of the absorption of the sample 32. The X-Y recorder 56 records the normalized measurements along a Y-axis as the light frequency control 58 changes the frequency of the monochromotor and shifts the recorder along the X-axis.

The light frequency control 58 effectively scans the monochromotor's spectral range slowly while shifting the X-Y recorder. According to another embodiment of the invention, the X-Y recorder controls the frequency control 58 as the recorder itself shifts along the X-axis. According to another embodiment of the invention, the function of the light frequency control 58 is performed manually.

The signal from the microphone 44 is proportional to the amount of light absorbed by the solid sample 32. Thus the resulting photoacoustic spectrum is very similar to the optical absorption spectrum.

It should be noted that the carbon black of the cell 26 absorbs uniformly over this whole spectral range. The circuit of FIG. 1 thus normalizes any spectrum obtained by dividing signals S1 and S2 in the divider 54. The use of separate lock-in or phase lock amplifiers 50 and 52 prevent phase problems resulting from the phases of signals from cells 1 and cells 2 being different.

Figure 5:
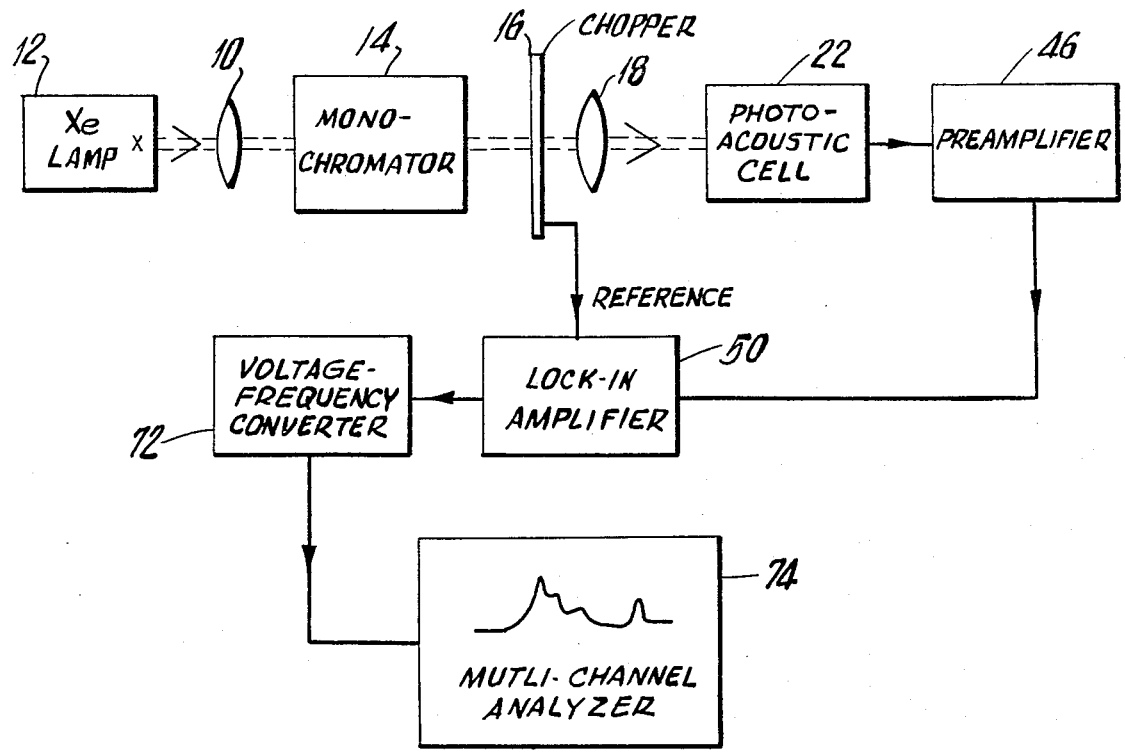
FIG. 5 is a partly schematic diagram of another system embodying features of the invention.

FIG. 5 illustrates another embodiment of the invention. This system is similar to that in FIG. 1. However, the output is not normalized. Here, the output beam of the monochromotor 14 passes directly through the chopper and the lens arrangement 18 to the cell 22 without passing through a beam splitter 20. Thus, the output of the lock-in amplifier 50 is not divided by the output of another lock-in amplifier. Rather, a voltage-frequency converter 72 such as a Vidar model number 241 digitizes the output of the lock-in amplifier 50 and converts the DC voltage to a series of pulses having a frequency proportional to the magnitude of the DC voltages. A multichannel analyzer 74 stores the pulses to produce a spectral output. A digital output at the spectrum can then be obtained on paper or magnetic tape. Here, the monochromotor is scanned along the light frequencies either manually or by a frequency control 58. Normalization can then be performed on a computer by dividing the digital spectrum of a sample by that previously obtained for a carbon black sample.

Figure 6:
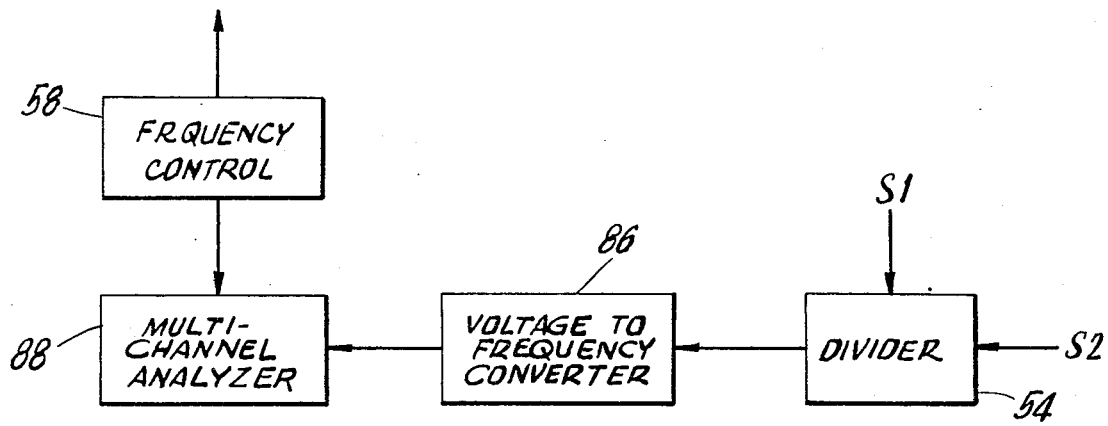
FIG. 6 is a block diagram of a modification of a portion of the circuit in FIG. 1, and embodying features of the invention.

FIG. 6 illustrates another manner of utilizing the output of the divider 54 of FIG. 1. Here, the normalized output from the divider 54 of FIG. 1 is digitized by a voltage-to-frequency converter 76 which passes the output to a multichannel analyzer 88. The frequency control 58 shifts channels. According to another embodiment of the invention, the frequency control 58 is omitted and the shifting accomplished manually.

The invention makes it possible to obtain energy absorption spectra on various solids. In particular, it makes it possible to obtain spectra on powders and other intractable solids which are either highly absorbing, highly reflecting, or highly scattering. Spectra can be obtained on inorganic solids, organic compounds, biological compounds, semiconductors, and metals.

Figure 7:
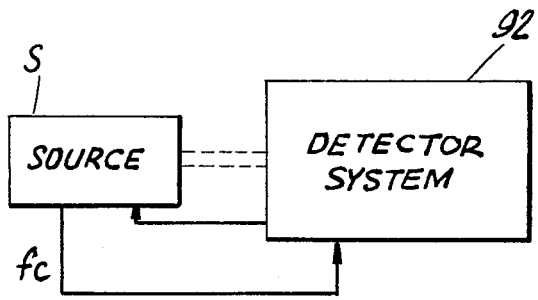
FIG. 7 is a generalized block diagram of a system embodying features of the invention.

According to the embodiment of the invention shown in FIG. 7, the scanning, varying source S composed of elements 10 to 18 in the system of FIG. 1 is replaced by other energy sources such as a source including an ultraviolet lamp which directs a beam to a detector system 92 which may be the remainder of the entire system of FIG. 1 or the remainder of the entire system of any of the other embodiments.

The extension of the ranges of the source frequency is made possible because the photoacoustic cell 22 is both the sample holder and the detector. Thus, the problem of adjusting the detector to the source is eliminated.

According to another embodiment of the invention, the source S includes a laser tunable to a multiplicity of discrete frequencies, or a dye laser which is tunable over a continuous spectrum. In such a source the laser replaces the elements 10 to 14. Where the laser is pulsed it also replaces the chopper 16.

According to another embodiment of the invention, the source S includes a Synchrotron which replaces elements 10 to 14. This is usable for studies with high energy photons (e.g. > 20 eV).

According to another embodiment of the invention, the source S is composed of two or more diode single frequency layer sources or lasers. The light frequency control shifts between the frequencies. The output is chopped or pulsed. Such a source is suitable where the entire spectrum need not be analyzed but only the relationship between responses of discrete frequencies is needed.

The invention can be used for scientific spectral analysis in any environment where a source of photons or other energy is available. According to an embodiment of the invention, the system of FIGS. 1 to 7 are used for quality control in manufacturing processes. This involves setting the monochromotor to one of several given wavelengths to monitor for purity or concentration. In these cases, source S may be in the form of dye lasers to increase sensitivity by increasing the amount of light available.

Figure 8:
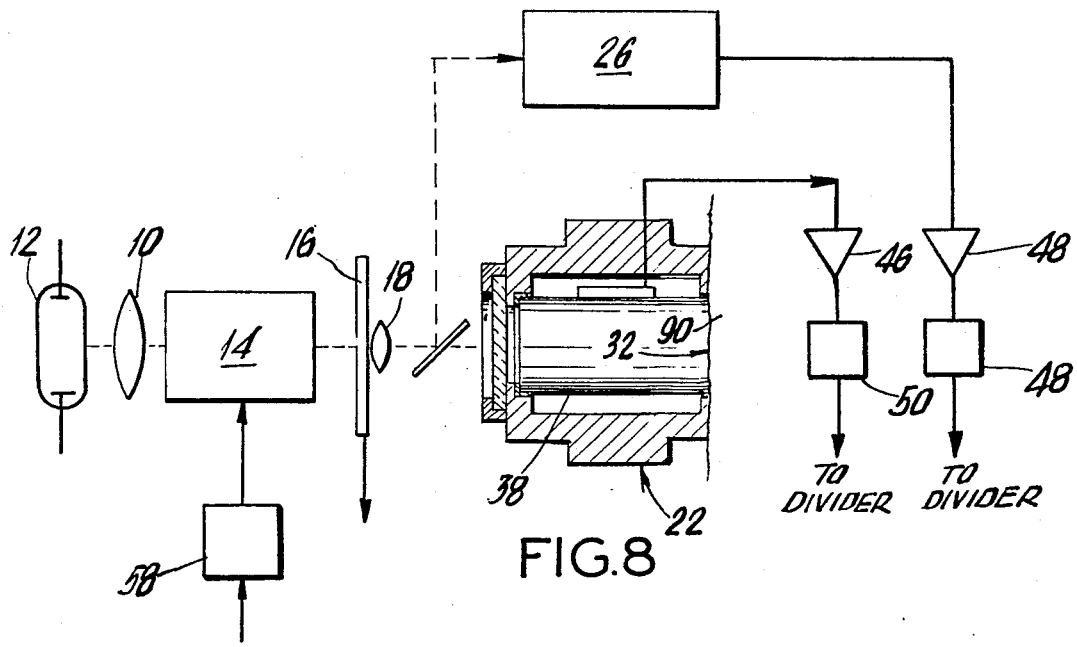
FIG. 8 is a partly schematic diagram of still another system embodying features of the invention.

Another embodiment of the invention is shown in FIG. 8. Here, the window 30 is eliminated and the tube 38 applied directly to the sample 32, which in this case is the skin 90 of a patient whose skin is being tested. The system of FIG. 8 otherwise corresponds to that of FIGS. 1, 5, 6, and 7.

Tests have been made on solid biological compounds such as blood and other substances of interest to the medical profession. It also permits a direct study of solid membrane materials such as bone, hair, and skin.

Figure 9:
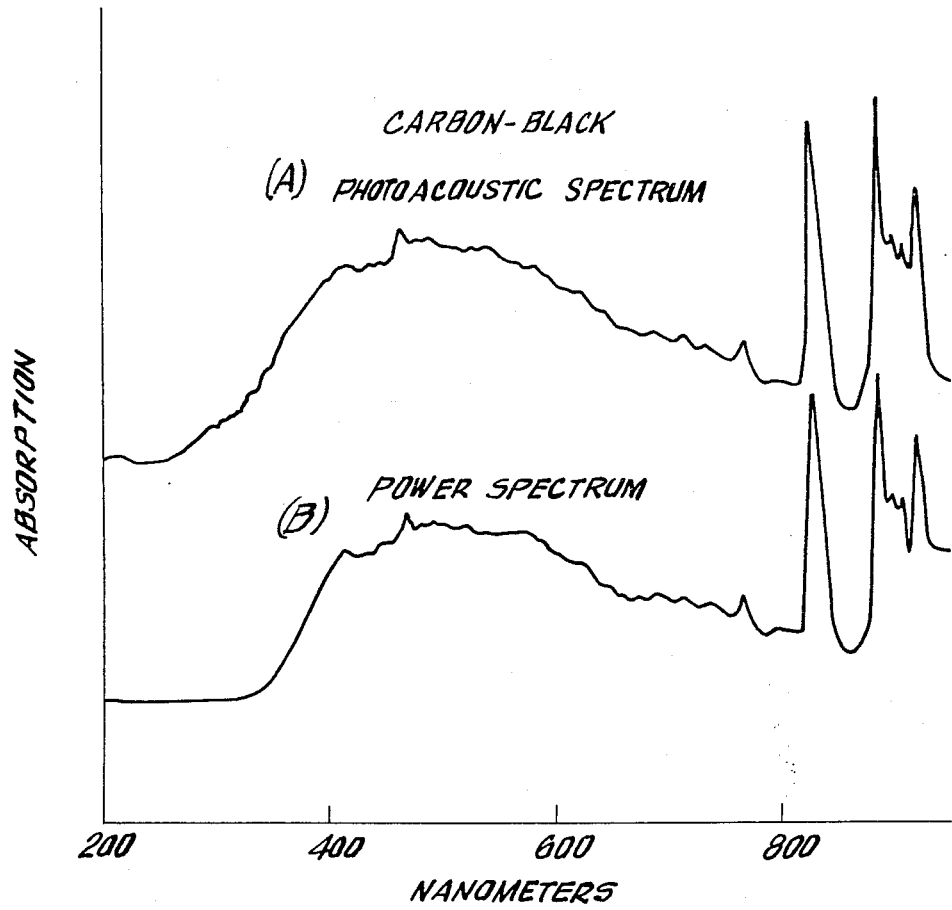
FIGS. 9 to 21 are graphs illustrating various response curves of the systems of FIGS. 1 to 8.

FIG. 9 is a graph illustrating the unnormalized photoacoustic spectrum of carbon black using the system of FIG. 5. The system of FIG. 1 can also be used by disconnecting the output of the lock-in amplifier 50 and connecting the lock-in amplifier 52 directly to the X-Y recorder 56. The carbon black spectrum is identified as curve A. A curve B in FIG. 9 illustrates the power spectrum of the lamp. The photoacoustic spectrum of carbon black is seen to be proportional to the power spectrum of the lamp. The power spectrum of the lamp was obtained with a silicon diode power meter. Above the 400 nanometer cutoff in the response function of the power meter, the two spectra are essentially identical. This, then, shows that the photoacoustic spectrum of carbon black as derived according to the invention is truly proportional to the power spectrum of the lamp. Therefore, the photoacoustic spectrum of carbon black can be used to normalize spectra.

Figure 10:
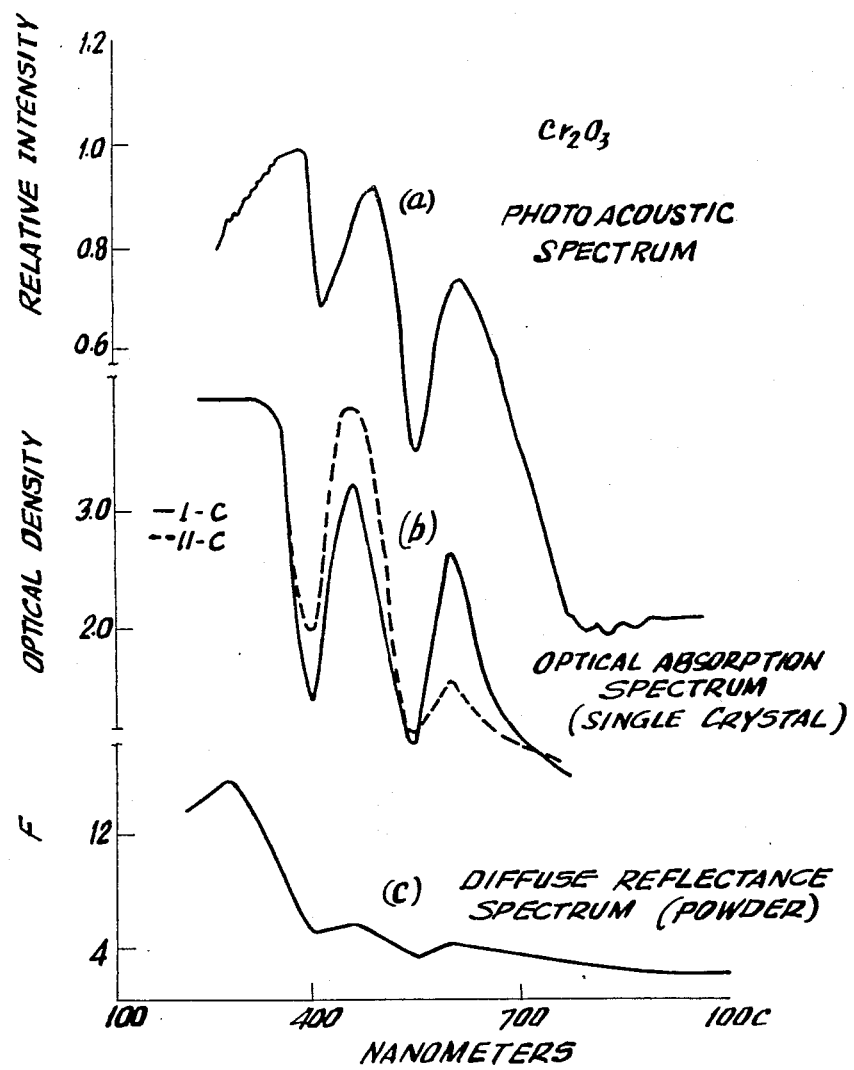

FIG. 10 illustrates three curves. The curve (a) of FIG. 10 shows the photoacoustic spectrum achieved with the system of FIG. 1 of polycrystalline $Cr_2O_3$ powder. Curve (b) is the optical absorption spectrum of a 4-micron thick crystal of $Cr_2O_3$ as obtained prevously by McClure. The bottom spectrum (c) is a diffuse reflectance spectrum of powdered $Cr_2O_3$ as obtained by Tandon and Gupta. The two crystal field transitions at 600 and 460 nanometers visible in the optical absorption spectrum are almost as clearly resolved in the photoacoustic spectrum of the invention, but not as clearly resolved in the diffuse reflectance spectrum.

Many inorganic and organic materials occur as polycrystalline powders. As such they cannot be readily studied by the usual optical transmission methods. At present, these materials are studied by diffuse reflectance methods. The spectrum of FIG. 10 shows that with the photoacoustic technique according to the invention one can easily and quickly obtain optical data of high quality on any type of polycrystalline or amorphous material.

Figure 11:
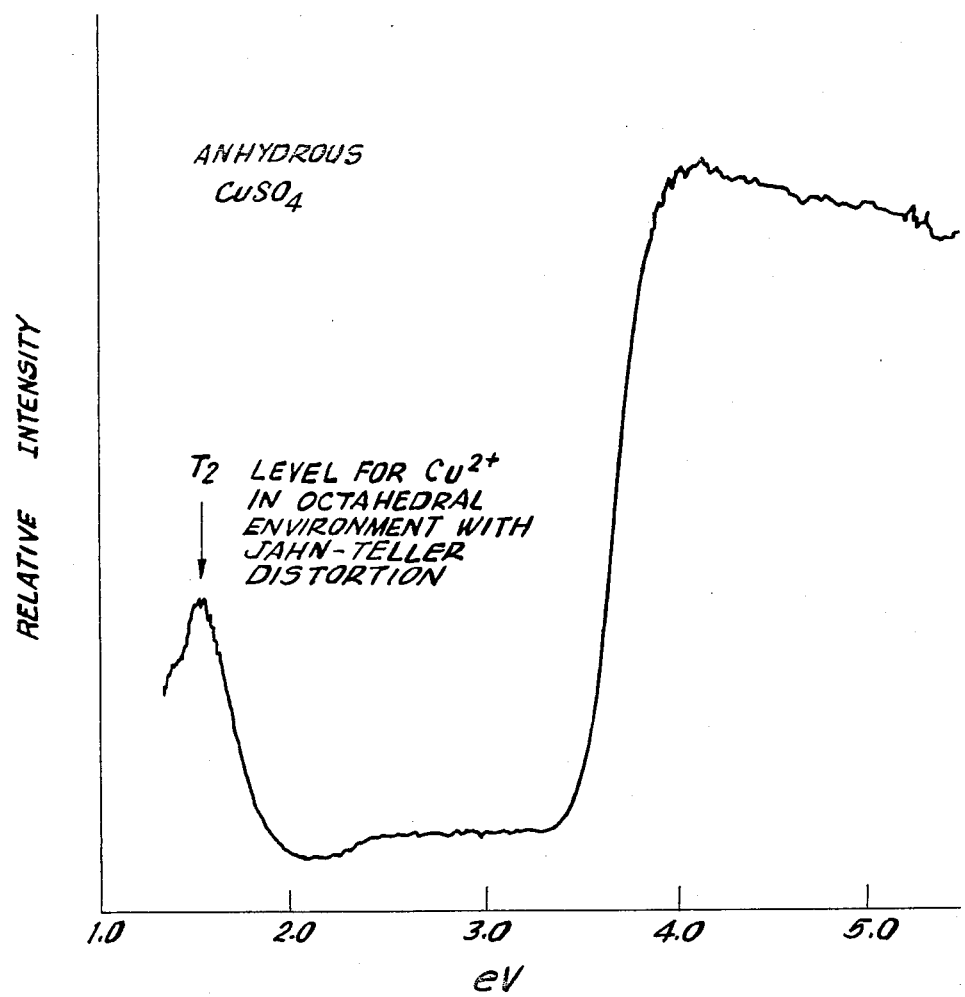

FIG. 11 is a photoacoustic spectrum, obtained according to the invention, of polycrystalline anhydrous copper sulphate powder. The arrow indicates the known position of the crystal field transition of $Cu^{2+}$ ion in copper sulphate. The peak in the spectrum corresponds to the arrow. The increased signal in the ultraviolet region represents the intense charge-transfer band in copper sulphate. This spectrum again demonstrates the usefulness of this technique in obtaining a spectrum on a polycrystalline inorganic insulator.

Figure 12:
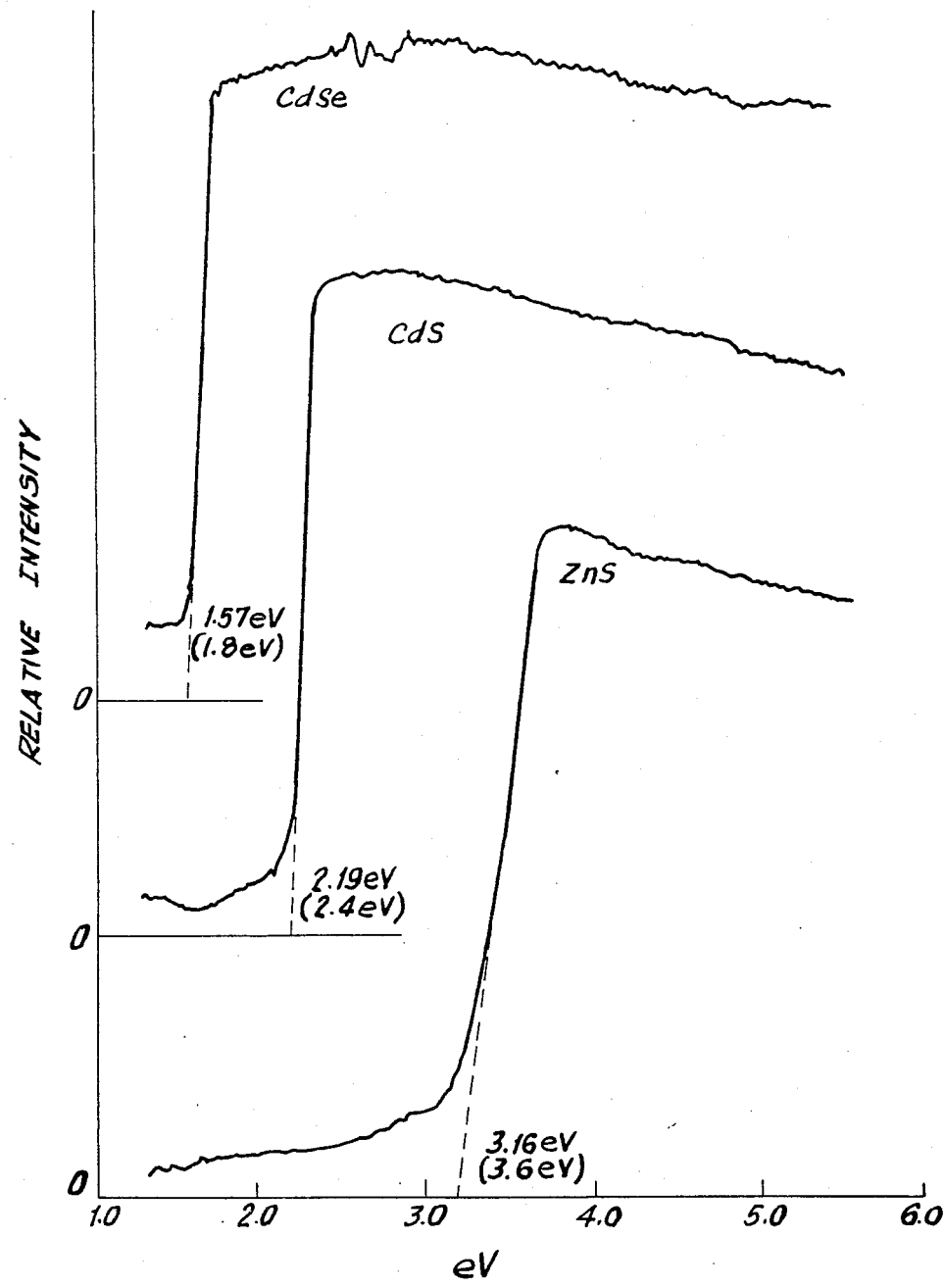

FIG. 12 illustrates the spectra, obtained according to the invention, of three inorganic semiconductors. All three were in powdered polycrystalline form. Ordinarily, optical data on semiconductors are obtained by reflection techniques requiring the presence of clean, smooth, highly reflective surfaces. According to the invention, spectra can be easily obtained on any type of semiconductor, whether it be a single crystal, polycrystalline powder or amorphous. Furthermore, if one uses the phase information available, one can also obtain optical data in the region above the optical band gap. This is possible because the phase information indicates how far the light penetrates into the solid.

Figure 13:
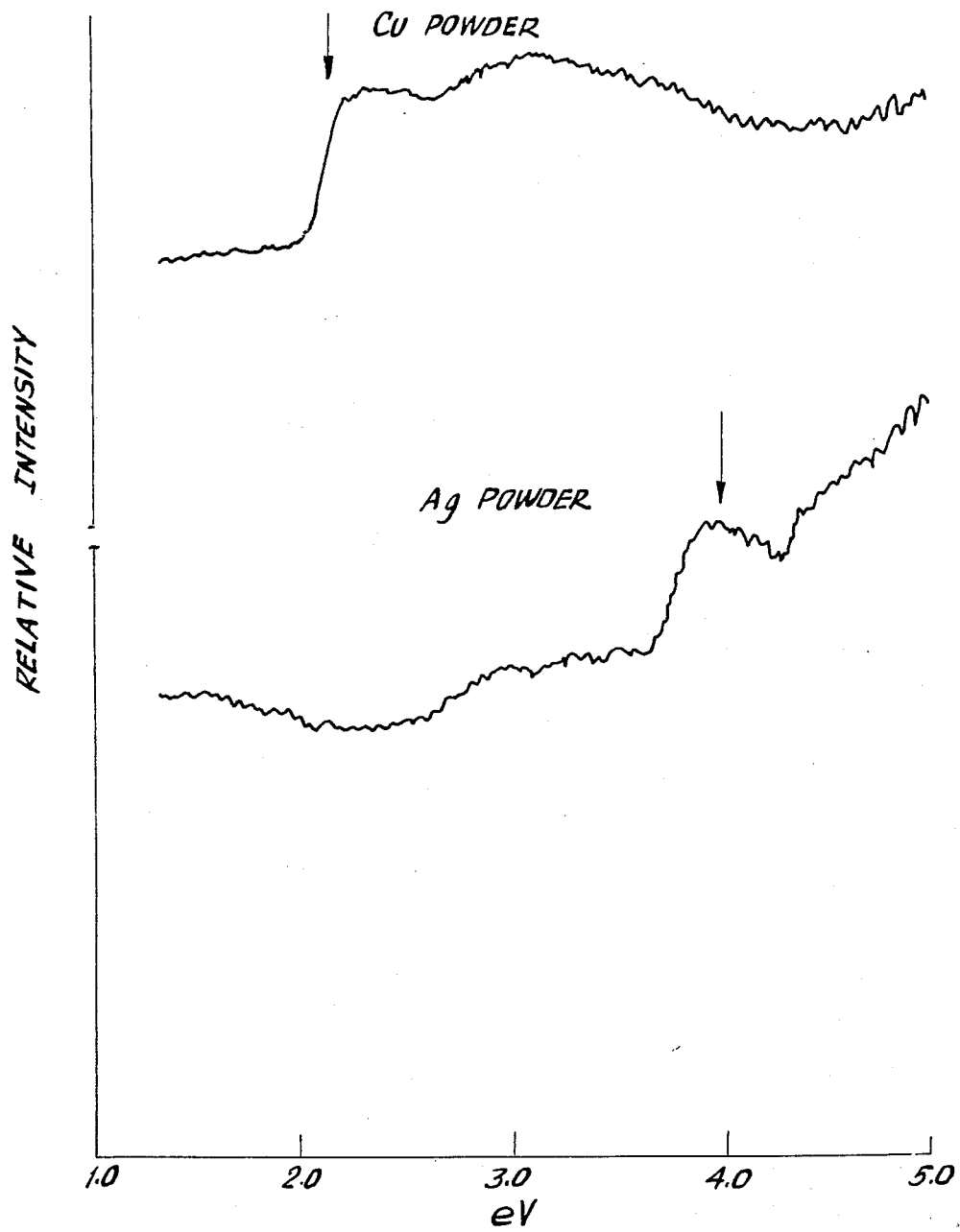

FIG. 13 illustrates the spectrum obtained on filings of copper and silver metal. This figure shows that the spectra according to the invention do not require good surfaces for obtaining clear detail on such highly absorbing and reflecting solids as metals.

Figure 14:
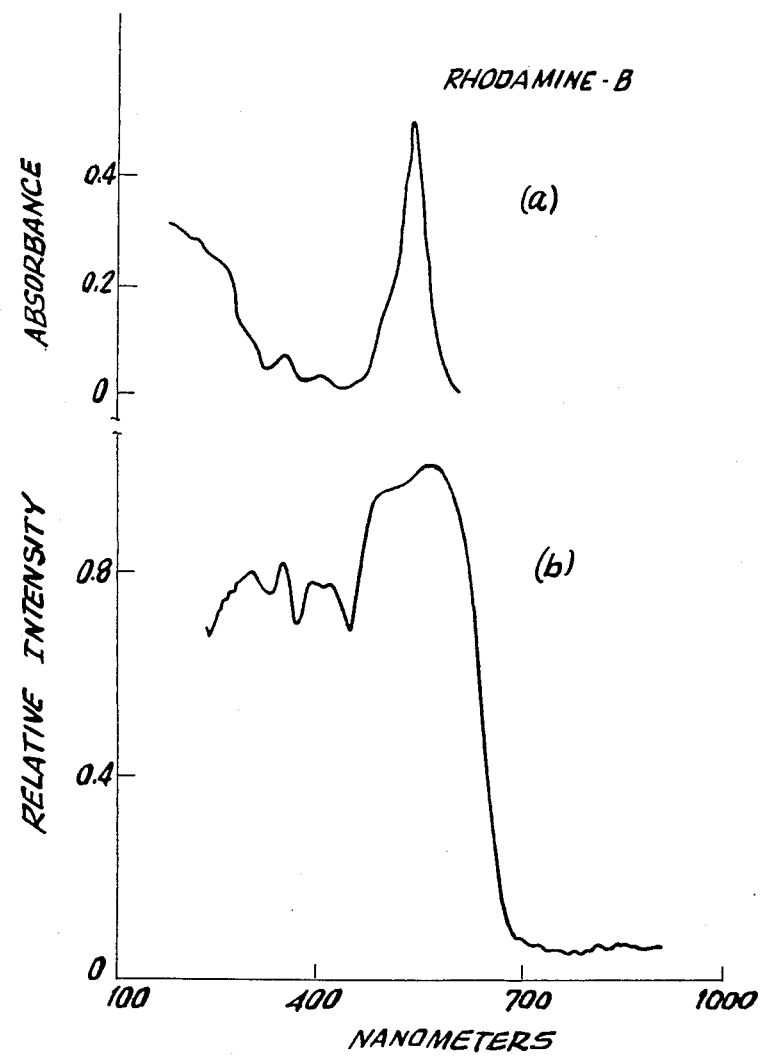

FIG. 14 illustrates the spectra obtained with the system of FIG. 1 of an aqueous solution of an organic dye, Rhodamine-B. This is shown by the curve at the top.

Figure 15:
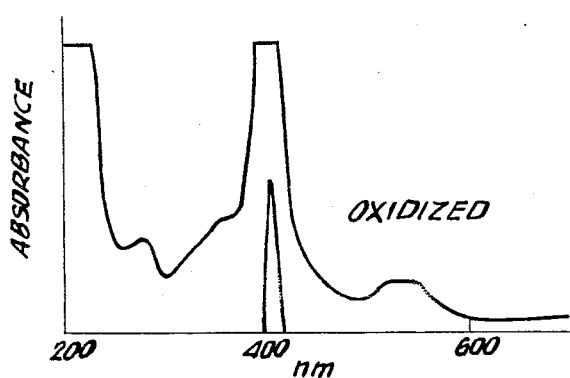
Figure 16:
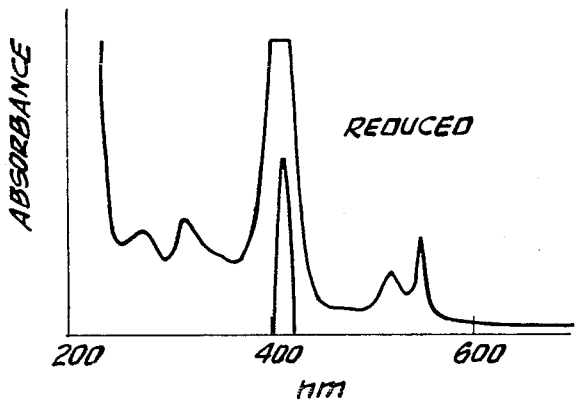
Figure 17:
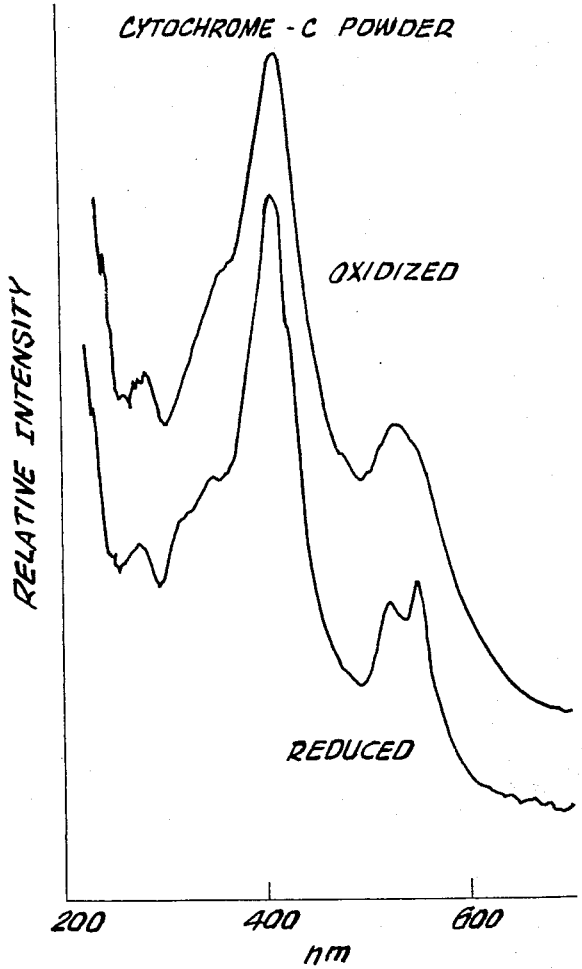

The lower spectrum is the photoacoustic spectrum of solid Rhodamine-B. As will be seen, the invention may be used to obtain optical data on organic compounds, even though they are a fine powder and very opaque. FIG. 15 and 16 illustrate prior art transmission spectra of an aqueous solution, Cytochrome-C which is an important respiratory protein. FIG. 17 is a photoacoustic spectrum of the same protein in solid form using the apparatus of the invention. FIG. 17 illustrates that the technique embodying the invention is capable of achieving at least the detail on the solid sample available in the past only on aqueous solutions.

Figure 18:
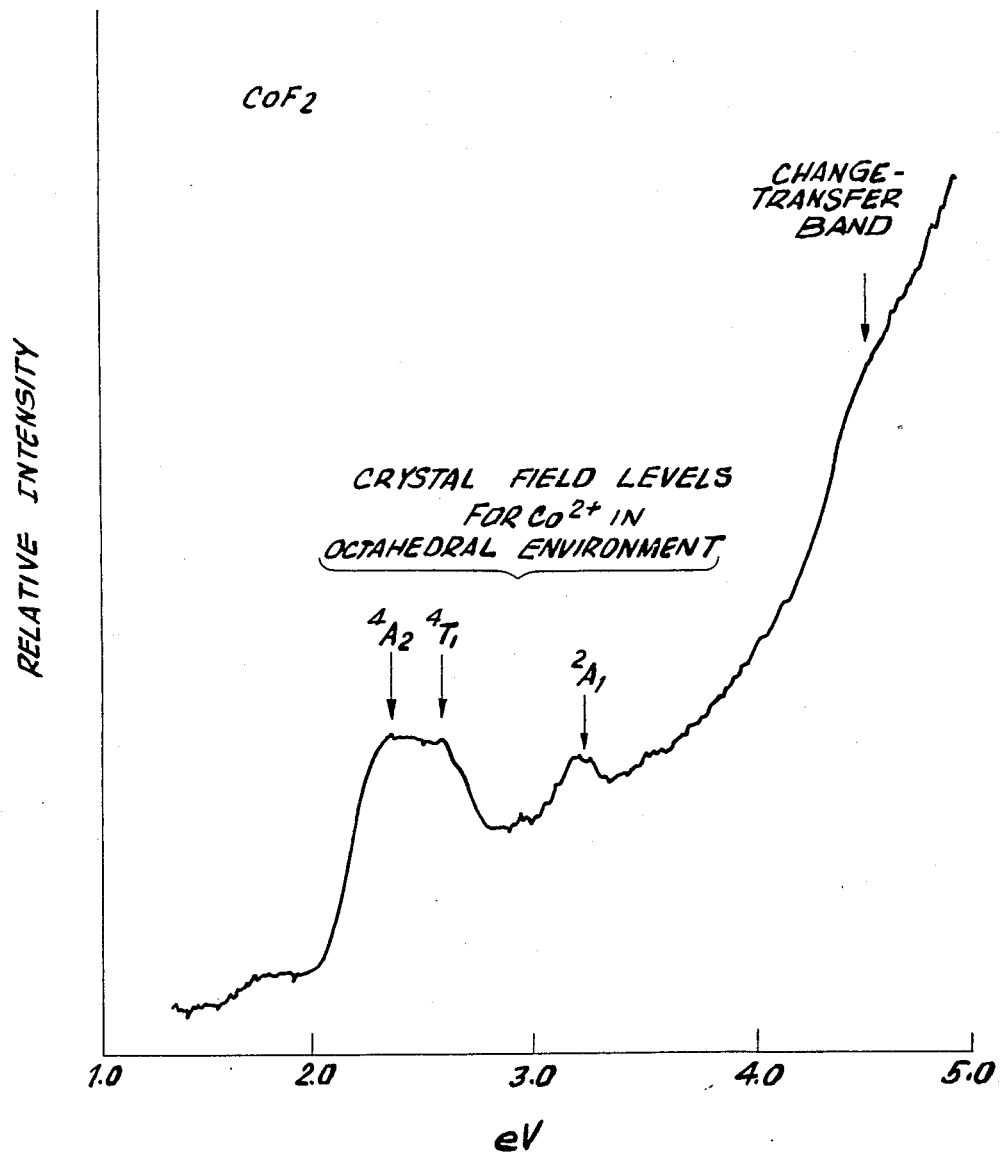

FIG. 18 is a photoacoustic spectrum of polycrystalline $CoF_2$ powder. The arrows represent the known crystal field positions of the $Co^{2+}$ ion in $CoF_2$. The Figure illustrates an example of the use of the technique according to the invention to obtain a spectrum of an inorganic insulator.

Figure 19:
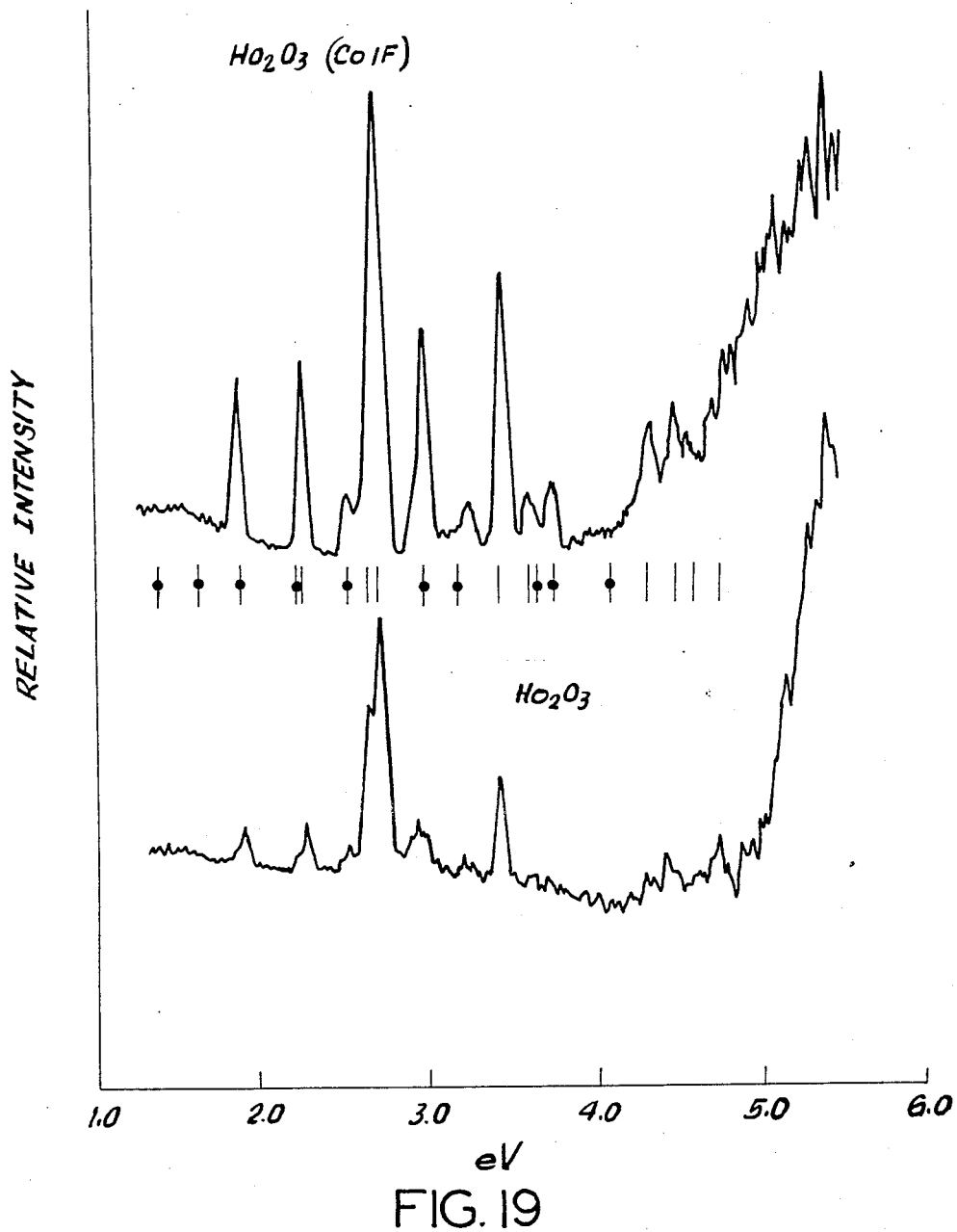

FIG. 19 illustrates the spectrum of $Ho_2O_3$ powder containing Co and F impurities. Several of the optical levels in $Ho^{3+}$ are normally fluorescent, that is these levels decay by the emission of a photon rather than by heating up the solid. The decay of a fluorescent level would then give only a week signal photoacoustically. In the top spectrum both the fluorescent levels indicated by the vertical line and the dot, as well as the non-flurorescent indicated by the vertical line, are present since the presence of the Co and F impurities inhibit the fluroescence. The bottom spectrum is of pure $Ho_2O_3$. Here, the relative intensity of fluorescent levels is greatly diminished. These graphs illustrate how sensitive the present invention is to the presence of fluorescence. Thus the invention can be used for studies on fluorescent materials.

According to an embodiment of the invention, the system is used for analyzing non-radiative decay processes in solids. This is particularly useful by using the phase information available. According to another embodiment of the invention, the non-radiative decay process is analyzed by studying the time evolution of the acoustic signal. Specifically, the microphone signal created by a flash lamp or pulse laser in FIGS. 1 to 8 is stored directly in a multichannel analyzer as it sweeps through the channels. The experiment is repeated many times to improve statistics and the information additively stored in the multichannel analyzer.

Figure 20:
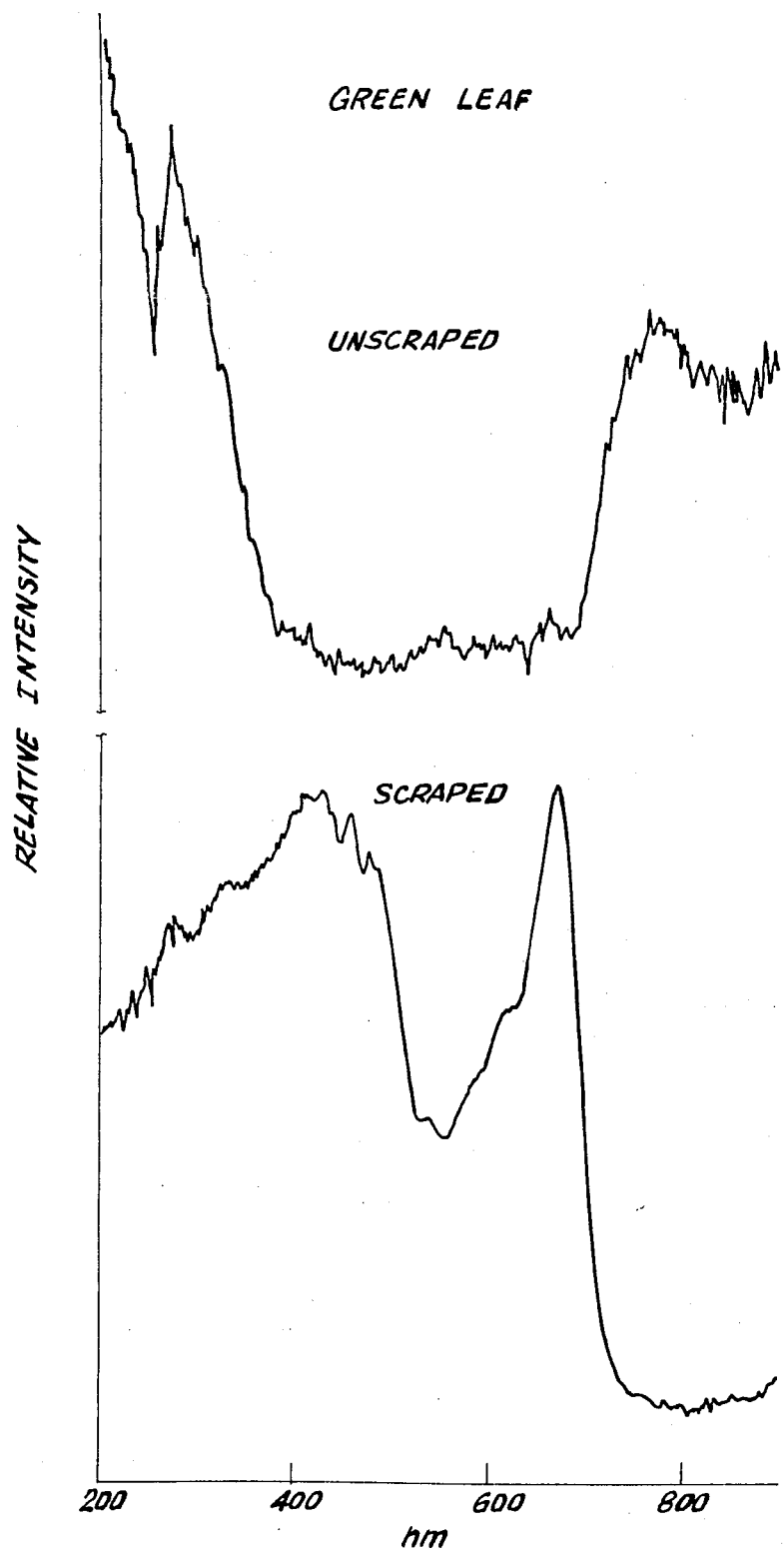

FIG. 20, at the top, illustrates a photoacoustic spectrum, achieved according to the invention by the system of FIG. 1, of the waxy matter at the surface of a leaf. The bottom curve is the photoacoustic spectrum of chlorophyl matter within the leaf. This experiment illustrates the usefulness of the present invention in obtaining high-quality optical data on intact living tissues such as plants. It permits study of plant life, the detection of plant disease and the study of the entire process of photosynthesis.

The invention contemplates studying not only solid substances themselves but quasi-solid samples, such as a liquid contained within a thin, solid membrane such as blood under the skin. The expression "quasi-solid" is intended to include such bounded liquids. The invention contemplates distinguishing between degrees of oxygenation of blood under the skin by comparing the spectra of blood of 1° of oxygenation with that of another, or by comparing portions of the spectra.

The particular embodiments of the invention are based partly upon the recognition that the chopped or pulsed light impinging upon the substance being tested produces in a part a cyclic heat flow out of the solid to the surrounding fluid, and that this heat flow produces a cyclic heating of a layer of nearby gas and this, in turn, acts as a source of sound waves. This recognition makes it possible to optimize the operation of the system.

The recognition that the heat flow exists contrasts with the possibility that gases adsorbed in the surface of the solid are driven off when a solid heats up and are readsorbed as it cools down. It also complements the possibility that the solid expands when it heats and contracts when it cools thereby producing a sound wave much as tuning fork does.

On the basis of this recognition, it was observed that the signal increases with the gas density and the sound velocity.

While embodiments of the invention have been described in detail it will be obvious to those skilled in the art that the invention may be embodied otherwise without departing from its spirit and scope.

The term quasi-solid as used herein is also intended to embrace viscous liquids such as drying blood. The invention has been used on bacterial samples for identifying bacteria.

Figure 21:
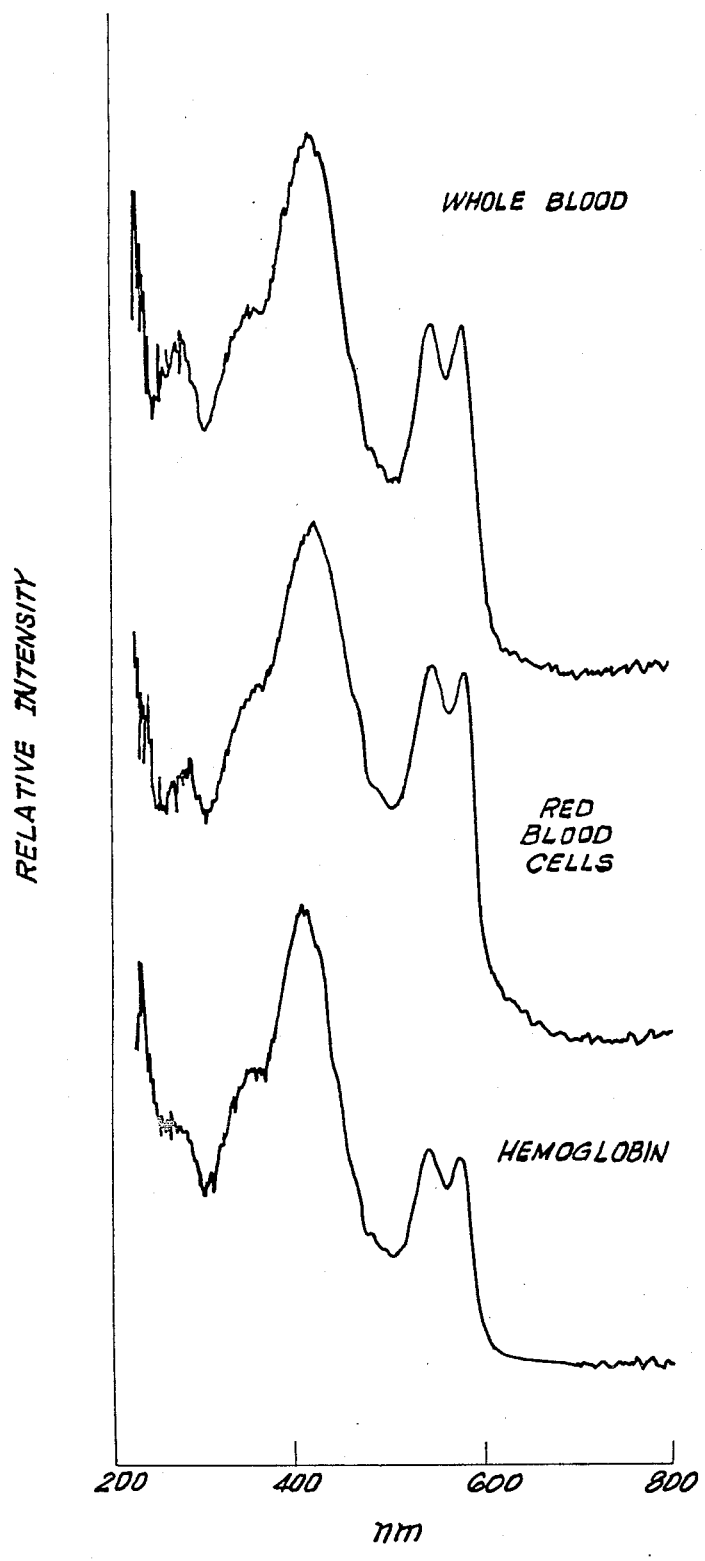

FIG. 21 shows photoacoustic spectra of smear of whole blood, red blood cells and of hemoglobin. The spectrum of whole blood is as clear and detailed as that of the hemoglobin extracted from whole blood. This is not the case in conventional spectroscopy. The invention thus makes possible the analysis of hemoglobin by analysing whole blood directly.

What is claimed is:

1. An apparatus for analyzing a solid or quasi-solid sample surrounded by fluid, including amplitude modulated energy source means for applying radiant energy of a predetermined frequency and periodically varying magnitude to the sample sufficient to produce detectable periodic variations which are indicative of the sample characteristic in the surrounding fluid, said source means including frequency varying means for varying the predetermined frequency of the energy which is applied, pickup means in the fluid and spaced from the sample for responding to the detectable variations in the fluid and producing electrical signals corresponding in amplitude and phase to the detectable periodic variations, said pickup means including means forming a chamber having internal walls which reflect both light and sound so that direct or scattered light does not strike an internal wall which can produce a detectable periodic variation and so that the chamber is susceptible of being a part of a high Q acoustic resonant system, said sample being located within the chamber, and means for indicating the intensity of the electrical signals at the different predetermined frequencies of the energy.

2. The apparatus as defined in claim 1, in which the indicating means includes means for sampling the electrical signals, said sampling means having an adjustable phase.

3. The apparatus as defined in claim 2 in which the chamber forms an acoustic resonator at the frequency of the periodic resonator.

4. An apparatus as defined in claim 3 in which the pickup means includes an electret microphone.

5. The apparatus as defined in claim 4 wherein the acoustic resonator includes said chamber and is in the form of a solid tube having a length equal to one-half the wavelength of the periodic variations.

6. The apparatus as defined in claim 5 wherein said microphone includes a foil electret mounted on said tube, said tube being composed of a metal and forming a capacitor electret microphone with said foil electret.

7. An apparatus as defined in claim 6 wherein said metal is selected from the group comprising aluminum and stainless steel.

8. The apparatus as defined in claim 6 wherein the surface of the tube under the electret is ridged to minimize the surface contact between the electret and the tube and thereby prevent the metal surface of the tube from producing the surface charge from the electret.

9. The apparatus as defined in claim 8 wherein the tube is perforated beneath the electret so that the electret responds to changes in pressure in the fluid in the tube.

10. The apparatus as defined in claim 6 wherein the electret microphone produces a maximum response at a frequency between 100 and 1,000 cycles per second.

11. The apparatus as defined in claim 1 wherein the fluid is maintained at a pressure above one atmosphere.

12. The apparatus as defined in claim 1 in which said pickup means forms only a portion of said chamber and said sample forms another portion of said chamber.

13. The apparatus as defined in claim 1 wherein said indicating means includes means for holding a black sample and for directing a portion of the energy with the varying magnitude onto the black sample, said indicating means including second pickup means corresponding to said first pickup means, and said indicating means including dividing means for dividing the output of said first and second pickup means so as to produce a normalized output at each energy frequency.

* * * * *